United States Patent [19]

Forbath

[11] Patent Number: 4,493,043
[45] Date of Patent: Jan. 8, 1985

[54] MEDICAL TIMING SYSTEM FOR USE DURING PREGNANCY AND METHOD OF USING SAME

[76] Inventor: Frank P. Forbath, 2880 Club House Rd., Costa Mesa, Calif. 92626

[21] Appl. No.: 325,037

[22] Filed: Nov. 25, 1981

[51] Int. Cl.³ .......................... G06F 15/20; G04F 7/06
[52] U.S. Cl. ..................................... 364/569; 368/251; 364/144
[58] Field of Search ................ 364/569; 368/110, 111, 368/112, 72, 73, 251, 63; 377/20, 26

[56] References Cited

U.S. PATENT DOCUMENTS

| | | | |
|---|---|---|---|
| 4,168,525 | 9/1979 | Russell | 364/569 |
| 4,223,379 | 9/1980 | Simcoe | 364/144 |
| 4,246,650 | 1/1981 | Moritani et al. | 368/111 X |
| 4,262,349 | 4/1981 | Sekiya et al. | 368/72 X |
| 4,276,541 | 6/1981 | Inoue et al. | 368/251 X |
| 4,276,610 | 6/1981 | Fleck | 364/144 X |
| 4,360,125 | 11/1982 | Martindale et al. | 364/569 |
| 4,367,051 | 1/1983 | Inoue | 364/569 X |
| 4,368,988 | 1/1983 | Tahara et al. | 368/63 |
| 4,382,688 | 5/1983 | Machamer | 368/251 X |
| 4,387,420 | 6/1983 | Singhi et al. | 364/569 X |

FOREIGN PATENT DOCUMENTS

2077005 12/1981 United Kingdom ................ 368/111

OTHER PUBLICATIONS

Programmable Event Timer, G. J. Stephens, IBM Technical Disclosure Bulletin, vol. 22, No. 2, Jul. 1979, pp. 785-786.
Timing Circuit Generates Selectable Clock Frequencies, F. Chitayat, Computer Design, Dec. 1979, pp. 104-107.

Primary Examiner—Edward J. Wise
Attorney, Agent, or Firm—Knobbe, Martens, Olson & Bear

[57] ABSTRACT

A medical timing system has a programmed computer controlled display and audible buzzer, with inputs from a timing switch and a readout button which are connected together so that pregnancy labor pains may be timed, contraction patterns may be rehearsed by an expectant mother, and fetus movements may be counted. The medical timing system is preferably handheld and compact so that the timing switch and readout button may be easily actuated and so that accurate and reliable timing measurements may be made and recorded through use of the system.

20 Claims, 3 Drawing Figures

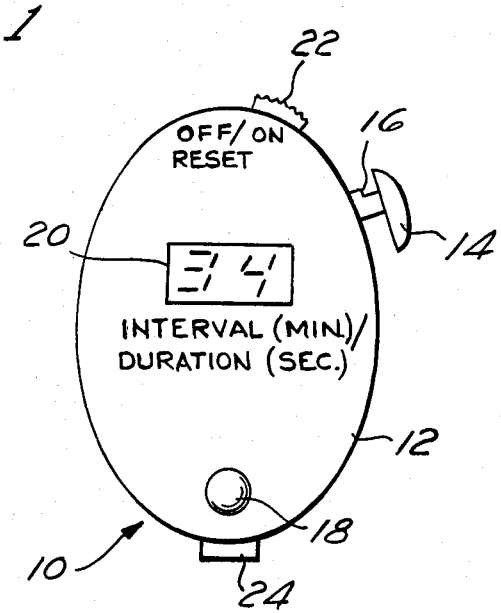

MEDICAL TIMING SYSTEM FOR USE DURING PREGNANCY AND METHOD OF USING SAME

FIELD OF THE INVENTION

This medical timing system for use during pregnancy is related to the field of diagnostic medical instruments and is more particularly related to electronic digital computer programmed devices for monitoring the occurence of biomedical events relating to childbirth and allowing the practice of procedures for natural childbirth.

BACKGROUND OF THE INVENTION

The timing of the interval between contractions during pregnancy labor has been used in the past in order to allow and expectant mother to determine when to call a doctor or go to a hospital. Such timing has been used by doctors and nurses in determining the proximity of birth. Thus, data on the time sequence of contractions—their duration and the interval between the successive start of each contraction—is an aid to the medical staff in determining the progress of labor and is a clue to when the expectant mother should go to the doctor's office for an examination or to the hospital for delivery. The measured durations and intervals aid in accurate determination of the apparent progress of labor. Additional clues—not used herein—to the medical staff on the progress of labor are the intensity of the contraction and the dilation of the cervix. In preparation for pregnancy labor, rehearsal techniques have been used (such as the Lamaze method) by expectant mothers and their coaches (typically the expectant fathers) in which a sequence of breathing exercises, message maneuvers, etc. of predetermined durations are performed in order to simulate the procedures for prepared childbirth. It is also known that the occurence of movements by the fetus indicates the health and state of development of the fetus.

A method for keeping track of labor contractions used in the past involved observing an ordinary wristwatch or stopwatch and manually writing down (as on pencil and paper) the times when contractions occurred. Often a coach would assist the expectant mother by observing the timepiece and writing down the times, since the expectant mother may be experiencing pain, loss of sleep, or may otherwise be incapable of making reliable measurements. However, the measuring ability of a coach who is fatigued or has lost sleep (which is often the case) may also be unreliable. This prior method has disadvantages in that manual subtraction computations are required (if an ordinary wristwatch is used) and the writing down of times requires light to see by (a disadvantage in the dark of night). Another inconvenience with this prior method is that a pencil, paper, and timepiece must be available at all times in order to measure and record the occurence of contractions.

A number of modern methods have been developed to assist expectant parents in preparing for childbirth. Such techniques as the Lamaze method may help provide for a more natural, painless childbirth. The natural childbirth methods may include rehearsal sessions in which the expectant mother (who is not then presently experiencing contractions) and a coach may go through a practice simulation of one or more of the phases of labor and the appropriate procedures. Such a rehearsal simulation proceeds in the classroom under the instruction of a training leader who announces, for a phase of labor, (at times chosen by the leader) the timing of labor contractions and describes the appropriate procedures so that the expectant mother and her coach may react and perform the procedures described. In order for the simulation to be realistic, it is preferable that the timing of the simulation should closely mimic the natural biological timing of labor. However, the timing of the simulation should not be so regular so as to allow the expectant mother or her coach to consciously or unconsciously anticipate the occurence of simulated contractions. The duration of the labor contractions and the time period between labor contractions are indicators of the progress of labor and as a predictor of when birth may be expected. Timing may be used in such methods to determine whether the expectant mother is experiencing the early, middle, or late phases of pregnancy. The phase of pregnancy, as determined by contraction timing, is used to guide the expectant mother so that preferred procedures (such as breath control exercises by the expectant mother, or specialized massages by a coach) may be performed at times appropriate to each phase of the pregnancy. After the birth has occurred, it may be important for the mother to regulate the duration of breastfeeding in accordance with instructions which may be given by a doctor to protect the health of the child and/or the mother. For example, it is desirable to prevent tissue irritation of the mother's breasts by limiting the feeding time, whil maintaining sufficient nutrition for the child.

SUMMARY OF THE INVENTION

The medical timing system of this invention is a biomedical instrument which acts as a guide in determining the time when birth is imminent, to aid the doctor in indicating the health of the fetus, for recording the activity of the fetus, and for providing the practice of natural childbirth procedures. The system includes a programmed digital computer processor for controlling the operation of the system and for providing a precise method of measuring and storing data relating to the occurrence of biomedical events. The program used for the processor allows the system to function in any one of three primary operating modes: a labor pain timer mode for recording the occurence and sequence of labor contractions, a fetus movement counter mode for counting the number of fetal movements during a time period, and a contraction rehearsing mode for simulating a series of labor contractions.

The system also has a manually operable timing switch connected electrically to the computer so that the user of the system may indicate to the system when biomedical events have occurred. The push button timing switch has a lock-down notch feature so that long duration time intervals may be measured without causing undue fatigue to the user of the instrument. The timing switch then may be released by a slight backward movement of the switch until the lock-down notch is released and a spring action of the timing switch pushes the switch upward to release the timing switch when the finger (thumb) is removed from the switch. The display may be used to present data relating to the mode of operation of the instrument, alerting signals, the occurrence and computations made by the system. A manually actuated readout button is also electrically connected to the computer and which serves to control the presentation of data in a display connected to the computer processor. The readout button and timing switch also serve to allow the user to select the operating mode of the system. The monitoring and training instrument of this invention is housed in a small, portable, hand-held housing which fits in the user's hand for easy operation.

During the labor pain timer mode, the computer processor of the system uses its random access memory for recording contraction time intervals and durations in response to actuation of the timing switch by the user (the expectant mother or her coach). The duration of a labor contraction is used in this description to mean the time period during which a labor contraction is felt by an expectant mother, and the interval of labor contractions is used in this description to mean the time period elapsed between the starting of one contraction and the start of the next sequential contraction. Once stored in memory, the time duration and interval measurements may be retrieved and displayed in the digital display so that medical personnel can analyze and evaluate the sequence of measurements to aid in determining the progress of labor. It is important that the contraction measurements be accurately made, stored and reproduced in order that the medical determinations be based on the valid measurements. The instrument of this invention is particularly effective in this regard in that the contraction duration and interval computations are made automatically and the measurements are reliably recorded for future evaluation. In practice, an expectant mother or her coach may operate the instrument in order to record the occurance of labor contractions, and the measurements so recorded may be transferred to a physician or other person for medical diagnosis. The transfer of the recorded measurements may occur by simply handing the instrument itself over to the medical personnel or through the use of a mode of indirect digital data communications. Because the measurement recording or storage is performed automatically by the instrument of this invention, it is inherently a more reliable process than the prior method involving the use of paper and pencil writings made by an expectant mother or her coach. The display of the instrument preferably produces its own light so that the instrument may be used in the dark, allowing the mother and father to sleep between contractions without having to turn a light on and off in order to record contraction times. Because the instrument is self-contained, the user need not continuously have available a timepiece, paper, and pencil as with prior methods of recording the occurrence of labor contractions or fetal movements. The simplified operation of the system lessens the chances or errors due to interruptions or distractions such as a telephone, doorbell, children's needs, etc. Because of the easy operation afforded by the construction of the instrument of this invention (especially the multi-purpose push-button timing switch and readout button), the instrument may be used by the expectant mother herself without requiring the help of another person. An anticipation alert warning is provided by the system (if the optional operation of the alert warning is selected) in advance of the time when a contraction may be expected so that she does not lose "control". If the anticipation alert warning is to be given, it is given in the embodiment shown herein at a time which is a predetermined anticipation time period (ten seconds) less than the immediately previously measure interval added to the time of starting the just previous contraction.

During the fetus movement counter mode, the computer processor of the system uses its random access memory to keep a count of the number of times that the timing switch is depressed during a time period. The system has a predetermined time period (twenty minutes) for counting, which may be shortened by the user through operation of the timing switch and readout button. The processor serves to compute the ratio of the number of fetal movements per unit time and to cause the results to be presented on the display connected to the computer. The system also allows the optional use of a buzzer connected to the computer in order to audibly indicate when the predetermined time period has elapsed. The purpose of monitoring the frequency of fetal movements in this mode is to indicate the health and activity of the unborn child, and to alert the expectant mother and her doctor to any unusual patterns of fetal activity.

During the contraction rehearsing mode, the processor of the system uses a stored pattern for simulated contractions from its read only memory. The simulated contraction pattern is randomized by the processor, and used to control the display connected to the processor so that the expectant mother and her coach may follow the simulated contractions. The system also allows the optional use of a buzzer connected to the computer in order to audibly indicate when the simulated contractions are to occur. The timing switch and readout button may be used together in order to allow the user to select from among three stored contraction patterns representing the early, middle, and late phases of pregnancy. The randomizing of the patten provided by the system is advantageous in providing some surprise to the expectant mother so that contractions are not anticipated. The fact that the rehearsing mode is easy to use and automatic is advantageous in increasing the likelihood that the expectant mother and her coach will perform the simulation techniques often. An optional breastfeeding timer mode may be used which allows the mother to select a set feeding time duration, and in which the processor presents a display of running time on a visual display and indicates when the set feeding time has elapsed so that the child's needs are met without undue irritation to the mother's breasts. An audible buzzer may be actuated for the processor in order to indicate running time and to indicate the end of the set feeding time duration.

DESCRIPTION OF THE DRAWINGS

FIG. 1 is a front view of the medical timing 30 system of this invention.

DESCRIPTION OF THE PREFERRED EMBODIMENT

Figure 2A:
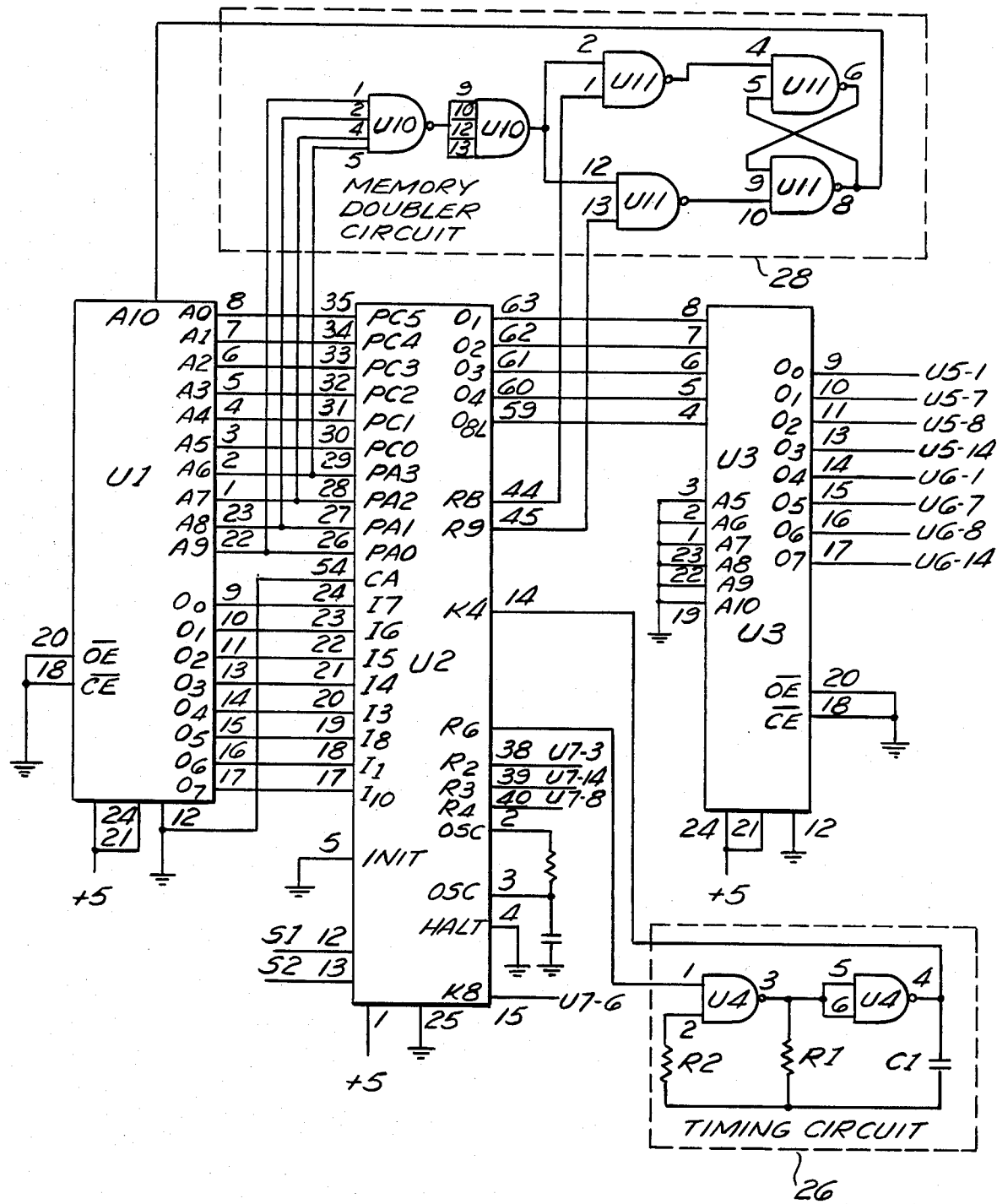
FIGS. 2a and 2b are an electrical schematic diagram of the electronic circuitry of the medical timing system of this invention.

Referring first to FIG. 1, the medical timing system 10 has an enclosure case 12 which is generally oval in shape and small in size so as to conveniently fit within the hand of a user. A manually actuatable timing switch 14 is positioned on the enclosure 12 so as to be easily and conveniently depressed by the thumb of the user when the enclosure 12 is held in the hand. The switch 14 includes a locking notch 16 mounted on the shaft thereof so that the switch 14 may be locked in a depressed condition by pushing downwards on the switch 14 and sliding the switch 14 forwards. The locking notch 16 of the switch 14 is similar in construction to the operation of locking pushbuttons used in commercially available home appliances, such as steam irons. The timing switch 14 is a manually operable swtich which is electrically connected to circuitry inside the enclosure case 12. The function of the swtich 14 is to indicate to the system 10, by means of external manual manipulation actuation by the user, the starting and stopping of labor contractions or the occurence of movement by the unborn child.

A display button 18 is provided on the face of the enclosure 12 in order to allow manual control over the functional mode of the system 10 and in order to control the nature of the information presented in a digital display 20. The readout button 18 is a manually operable electrical switch which is connected to circuitry inside the enclosure case 12. The timing switch 14 and readout button 18 are to be used together, cooperatively, to allow manual selection of the functional mode of the medical timing system 10. The display 20 is preferably a light emitting diode array having two seven segment digits and a decimal point after each of the digits. Although a liquid crystal type display could be used, it is preferable that a light emitting diode type be used in order that the display 20 provide it's own illumination for night time viewing, or that if a liquid crystal display is used, that illumination be provided by a separate internal light source.

As an alternative version, a pair of displays could be used to replace display 20 so that simultaneous display of two related types of data (such as measured labor contraction duration and interval) would be presented.

A power control switch 22 is provided on the enclosure 12 in order to connect batteries inside the enclosure 12 with electronic circuitry inside the enclosure 12, and in order to allow the electronic circuitry inside enclosure 12 to be reset to an initialized condition when the switch 22 is placed in an off position. The system 10 may be equipped with an external power source connector 24 which allows the batteries inside the enclosure 12 to be recharged through an external power source (not shown) such as a battery charger connected to an AC utility line.

In practice, the enclosure 12 is grasped in the hand of the user, who may be either the expectant mother or coach. The switch 22 is placed in an on position and the thumb of the user is utilized through control the timing switch 14 in order to record the times when labor contractions start and stop, or when movements of the unborn child are detected. The switch 14 is to be depressed when a contraction starts, held in a depressed condition for the duration of the contraction until the contraction stopped, and then returned to an undepressed position when the labor contraction stops. The readout button 18 is used in order to control the operation of the system 10 so that data stored inside the enclosure case 12 may be presented in the display 20.

Figure 2B:
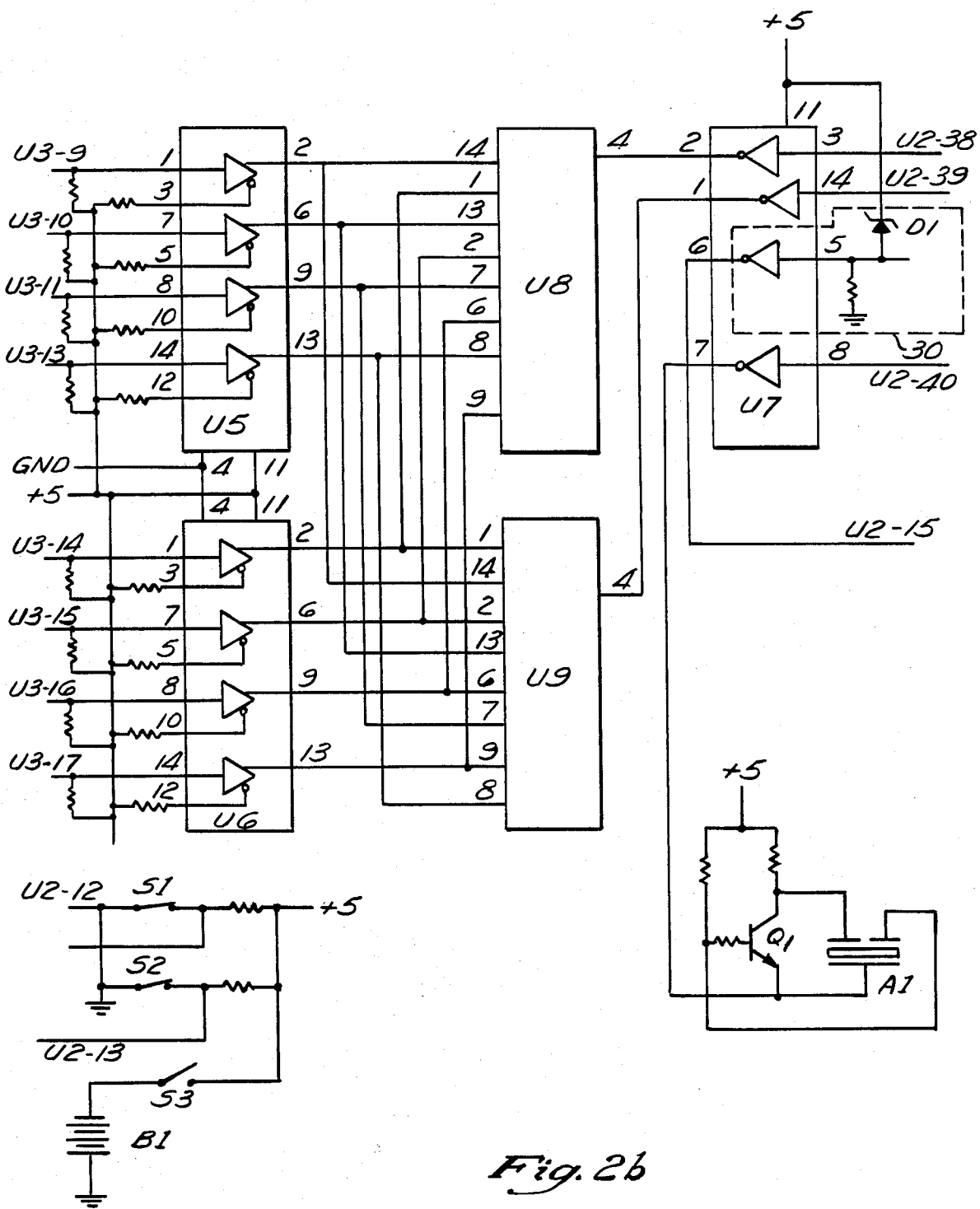

Referring next to FIGS. 2A and 2B, the electrical circuitry of the system 10 inside the enclosure case 12 is shown. The circuitry includes the following commercially available integrated circuits:

| Number | Type | Description |
| --- | --- | --- |
| U1 | 2716 | Erasable Programmable Read Only Memory (EPROM) |
| U2 | TMS1099JLC | Microprocessor |
| U3 | 2716 | Erasable Programmable |

| | | -continued |
| --- | --- | --- |
| Number | Type | Description |
| | | Read Only Memory (EPROM) |
| U4 | CD4011 | Dual Nand Gates |
| U5 | 75491 | Quad Display Driver |
| U6 | 75491 | Quad Display Driver |
| U7 | 75492 | Quad Inverters |
| U8 | MAN84A | Seven Segment LED Display |
| U9 | MAN84A | Seven Segment LED Display |
| U10 | 74C20 | Dual Nand Gates |
| U11 | 74C00 | Quad Nand Gates |

In FIGS. 2a and 2b, pin numbers of each of the integrated circuits are shown adjacent to the integrated circuit symbols. Connections made between integrated circuits on the two figures (2a and 2b) are shown as the circuit number, followed by a dash, followed by the pin number to which connection is made. The microprocessor U2 is a programmable digital computer processor having internal random access memory and which is commercially available from Texas Instruments, Inc. of Dallas, Tex., U.S.A. The memory U1 is used to store the object code computer program which is disclosed herein and which is used to control the operation of the microprocessor U2. The memory U3 is used to decode the information output from the processor U2 in order to properly drive the displays U8 and U9. The gates of U10 and U11 form a memory doubler circuit 28 used to effectively double the memory addressing capacity of the processor U2 in addressing the memory U1. The circuits U5 and U6 are connected between the processor U2 and the light emitting digital displays U8 and U9. The gates of integrated circuit U4, together with a capacitor C1 and resistors R1 and R2 form a timing circuit 26 which is adjusted (by changing R1, R2 and C1) to produce pulses every one-sixteenth of a second (62.5 milliseconds) that are used by the processor U2 to keep track of time using well known programming techniques. Of course, the timing circuit 26 may be replaced by circuitry which senses a powerline frequency (such as 60 Hertz), or may be replaced by software steps which keep track of time delays or sequences of operations which are related to the cycle of time of the processor U2. A digital output (not shown) may be connected to the processor U2 in order to allow the system 10 to be connected through a digital data communications system in order to transfer the information collected by processor U2 to larger data processing systems. Such larger data processing systems may include centralized patient monitoring consoles at which a nurse may simultaneously monitor the status of several expectant mothers so that medical personnel may be dispatched and care provided when needed. The integrated circuit U7 is connected to the processor U2 in order to control the displays U8 and U9, to sense when the power supply (battery B1) voltage is low by using the voltage sensing circuitry 30 which includes zener diode D1, and to control actuation of the audible buzzer A1 through the transistor Q1. The switches S1, S2, and S3 shown in FIG. 2B correspond to timing switch 14, readout button 18, and power control switch 22 of FIG. 1, respectively.

The description presented herein shows a system 10 using a TMS1099JLC microprocessor U2 available from Texas Instruments, Inc. of Dallas, Tex., U.S.A. Such as system 10 requires that read only memory program storage devices be programmed for the labor pain timing mode and the rehearsing mode or for the labor pain timing mode and fetus movement counter mode; inasmuch as the program coding for all three modes is too voluminous for use with the TMS 1099 JLC microprocessor U2 because of addressing limitations with that device. An alternative embodiment for the invention may be constructed by replacing memory U1 with a pair of type 2716 read only memories having all inputs (A0–A10) and outputs (00–07) connected in parallel. Such a pair of read only memories would be selectively connected to provide information to the processor U2 through actuation of a toggle switch. The output enable (pin 20) and clip enable (pin 18) control lines of the type 2716 memories would be connected to the toggle switch so that only one of the memories would supply information to the processor at one time. The toggle switch would be mounted on the enclosure case 12 for manual actuation by the user. When the toggle switch is in its first position, the first alternative embodiment type 2716 memory (having code for the labor pain timer mode and code for the fetus movement counter mode) would be activated to provide programming for the processor U2. When the toggle switch is in its second position, the second alternative embodiment type 2716 memory (having code for the labor pain timer mode and code for the contraction rehearsing mode) would be activated to provide programming for the processor U2. Thus the user would place the toggle switch in its first position to allow contraction timing or fetal movement counting, and would put the toggle switch in its second position to allow contraction timing or a rehearsal of contraction simulations. A further embodiment of the invention may include a microprocessor and memory having sufficient capacity or arranged in such a way as to have coding for all three modes without requiring a manual toggle switch.

Included as a part of this specification are twenty-nine pages of computer printout sheets which form a listing in the Program Design Language (PDL) which describes the functional operation of the computer program of this invention in conformance with the guidelines described in the U.S. military specification MIL-STD-1679. The PDL listing is not a computer program itself and is not intended to be assembled or compiled into machine instructions. However, the PDL listing may be used as an aid by a computer programmer in writing a computer program for use in this invention. The object code computer program listing presented later herein used the functional approach disclosed in the PDL listing below.

Page 1 of the PDL listing is a table of contents for the PDL listing which describes the parts of the listing, including the five flow sections: Initialization, Labor Pain Timer Routines, Readout and Labor Pain Announcer, Labor Pain Rehearsing Routines, and Fetus Movement Counter Routines. After the five flow sections, the PDL listing includes cross-referencing tools which aid in the understanding of the PDL listing; i.e., a Data Index, a Flow Segment Index, and Segment Reference Trees. The PDL listing may be used in much the same way as computer program flow chart drawings have been used in the past in order to understand the functional operation steps performed by the invention, and the sequence in which the steps are performed.

The pages of the five sections of the PDL listing have a heading indicating the section name and page numbers, and subsection name unique to the page describing the functions performed by the subsection shown on the page, and have five vertical columns: a universal line number (ULN) column; a reference page column; a local line number column; and a listing text column. Separator pages (pages 2, 5, 9, 12 and 16) are provided before the start of each section of the PDL listing. The universal line numbers describe the position of each line of text with respect to the start of the entire listing, and the local line numbers describe the position of each line of text with respect to the start of each page (for example, on page 6 of the PDL listing, the universal line numbers span from 45 to 69 and the local line numbers span from 1 to 25. The reference page column lists the page at which a reference made in the PDL listing text may be found (for example, on page 6, universal line number (ULN) 65, a reference is made to "TIMIN" which may be found on page 7 (ULN 71) of the PDL listing). The text of the PDL listing is broken up into functional flow portions which are preceded by a label which is denoted by a subsequent colon, such as the three flow portions on page 6, denoted with the segment name, "Perform Labor Pain Timing Mode," of the PDL listing which are labeled NO SWITCH, LOOP B0, and LOOP B1. Nonfunctional, explanatory comment entries in the PDL listing are denoted by text preceded by pairs of periods, such as the text at ULN 155 on page 10 which noted "READOUT RELEASED."

Starting with page 20, an index is presented of various data items which are used as counters and the like in the PDL listing. The index is a list in which the name of each data item is preceded by the initials "DI", and in which the PDL listing pages on which the data item is referenced are placed below the data item name. After each page number in the data item listing, a functional description (the flow segment name) is presented to show how the data item is used on that page of the PDL listing, and underneath the description, the local line numbers at which the data item is referenced are presented. For example, on page 20.001 of the PDL listing, it is shown that the data index "Practice-Pattern" is used in performing the rehearsing mode flow segment at local line numbers 2, 4, 24, 25 and 26 of page 13; and is used in the output contraction data flow segment at local line number 1 of page 14.

Beginning with page 21, an index to the flow segments is presented in which the name of each flow segment is preceded by the page on which the segment appears in the PDL listing, and the letters "FS". Underneath each listed flow segment name in the index, the page number and referencing segment name of each flow segment in which the listed segment is referenced are presented. The local line numbers in which the reference is made in the referencing segment are listed under the referencing segment name. For example, the flow segment on page 4 ("Initialize Labor Pain Timer") is referenced by the local line number 16 of the flow segment on page 3 ("Power On Initialization"), as detailed at the top of page 21.001.

Referring next to page 22.001 of the PDL listing, a set of flow segment reference trees is presented in which three columns are presented: a logical segment number column, a defined segment number column (corresponding to the page number), and a flow segment name column. The tree has three major branches (shown at logical segment numbers 2, 14, and 17) which correspond to the three operating modes of the invention and which are denoted "Initialize Labor Pain Timer", "Perform Fetus Movement Counter Mode", and "Perform Rehearsing Mode". The segment reference tree shows, in a hierarchical fashion, the referencing which occurs between the flow segments representing the sequencing of operations performed by this invention. Flow segments which are used more than once in the PDL listing tree are preceded by a star or a dash and are followed by the logical segment number where first used (for example, at logical segment number 11, the flow segment "Perform labor Pain Timing Mode" is used, and which was first used at logical segment number 5). The flow segment reference tree shows, in an indented outline format, the sequences in which the PDL listing segments may be referenced. For example, since the segments "Perform Labor Pain Timing Mode" (logical line number 7) and "Monitor Timing Switch" (logical line number 8) are both indented beneath the segment "Perform Labor Pain Announcer Mode" (logical line number 6), either of the segments (logical line numbers 7 or 8) may be referenced from the segment at logical line number 6.

INITIALIZATION

When power is first applied to the circuitry of this invention (as by operating switch 22), operation of the program begins as described on page 3 of the PDL listing. The first operation performed on initialization (as shown at ULN15) is to set all of the circuitry to predefined initial conditions. If the voltage of the battery B1 is low, the display 20 is caused to flash a display symbol "LO". If the voltage of the battery B1 is not low, the display 20 is caused to flash a decimal point momentarily. The display 20 is used in the system 10 to present displays representing measurements and computations made by the system 10, and in order to acknowledge the operating status (such as the modes and features described herein) of the system 10.

The way in which the user of the system 10 selects the operating mode is outlined in ULN 23-30 of the PDL listing. Actuation of the timing switch 14 and the readout button 18 serves to select the mode of the system 10. The conditions of the switch 14 and button 18 are determined by the microprocessor U2 under control of a computer program which operates as described in the PDL listing. Although not specifically described in the PDL listing, time delays and rechecks are used by the steps shown at ULN 23-30 to make sure of the status of the switch 14 or button 18 and avoid errors due to switch contact bouncing. Also, the steps at ULN 23-30 allow a short period of time during which a user may actuate both switch 14 and button 18 in mode selection. If neither timing switch 14 nor readout button 18 is actuated, the steps shown in ULN 31-35 are performed so that the display 20 continues to show either "LO" or a flashing decimal point (depending on the voltage of battery B1) until either the switch 14 or button 18 is actuated. If the timing switch 14 alone is actuated, the medical timing system 10 will be placed in the labor pain timer mode (the description of which starts on page 4 of the PDL listing). If the timing switch 14 and readout button 18 are both actuated substantially simultaneously (and remain actuated for a short time), the fetus movement counter mode is entered (see page 17 of the PDL listing). Finally, if the readout button 18 alone is actuated, the contraction rehearsing mode is entered (see page 13 of the PDL listing). Once an operating mode has been selected by the switch 14 and button 18, the power to the microprocessor U4 must be cycled (on-off-on) through the use of the power control switch 22 in order to end the mode in use and select another mode.

LABOR PAIN TIMER MODE

Description of the labor pain timer mode begins on page 4 of the PDL listing. After the initialization of the medical timing system 10 as described above, and the selection of the labor pain timer mode through the actuation of the timing switch 14 alone, the current time is saved by the microprocessor U4 and the display 20 shows an "8.8." test pattern for one second in order to allow the user to verify that the display 20 is operating properly.

The processor U4 then initialized the contraction time count (at ULN 40) to one second, sets a flag to indicate first time, and sets a counter to one to indicate how many times the timing switch 14 has been depressed. This last operation of keeping track of the number of times that the timing switch 14 has been depressed is used to allow the labor pain announcer feature of the labor pain timer mode to be turned on and off by depressing the timing switch 14 for three times in a quick sequence, as will be described below. The computer program of this invention then jumps into a normal timing switch routine on the PDL listing page 7 at a special entry point (labeled FIRSTC) to bypass some operations the first time (PDL listing page 7, ULN 73).

On page 7 of the PDL listing, the normal timing switch 14 depression (after the first time that switch 14 is depressed) saves the current time (from the internal timekeeping routine of the software program which samples the timing pulses produced by timing circuit 26) as the start of contraction and sets the running counter (CONTRACTION-TIME) to zero (ULN 72). These operations are also indicated on page 4 of the PDL listing for use during the first loop of the routine, and thus those related steps on page 7 are bypassed during the first time through the routine.

On page 7 of the PDL listing, ULN 74-77 present the running time in the display 20 for a 250 ms duration during the contraction measurement. Running times greater than 99 seconds have the right hand decimal point lit in the display 20 to show the overflow. ULN 78-95 implement a waiting loop for a timer clock in the software program to tick over to the next integral second. The timer clock in the software program of this invention keeps a count of the timing signals received by processor U2 from the timing circuit formed by the gates of circuit U4. During this waiting time, the timing switch 14 is checked to make sure that the timing switch 14 is held in a depressed condition. Note that the timing switch 14 is to be held in a depressed condition during the time that a contraction is proceeding when the system 10 is in a labor pain timer mode. The timing switch 14 is to be left in an undepressed condition during the interval between contractions. When in the labor pain timer mode, the processor U2 keeps a record in its random access memory of the time of starting and stopping of each contraction so that such data may be processed to determine the time duration of each contraction, and to determine the time interval between sequentially adjacent contractions. If during the waiting loop shown at ULN 78-95, the timing switch 14 is released from its depressed condition, an exit is made to process and record the interval and duration information, as shown in page 8 of the PDL listing. If the timing switch 14 remains in a depressed condition during the waiting loop, the software timer clock is checked. When an integral second of the software timer clock has elapsed, the time count (CONTRACTION-TIME) is incremented, and tests are made inside the waiting loop in order to determine the type of presentation to make in the display 20. The intent of the tests made inside the waiting loop of ULN 78-95 is to cause the display 20 to present a running time indication on the second up to eleven seconds, and thereafter to present the running time every five seconds, with decimal points flashing for the intervening integral seconds. Thus, when in the labor pain timer mode, the display 20 is actuated by the processor U2 to present a visual display of the running time duration of the contraction. If the timing switch 14 is held down for more than 180 seconds, the display 20 ceases to present the running time.

When the timing switch 14 is released, thus indicating that the labor contraction has ended, the "process new interval" segment is entered on page 8 of the PDL listing. A test is made at ULN 98-109 to determine if the duration of the contraction just measured was less than a predefined minimum duration (23 seconds), and if so, the measured contraction is not considered to be a valid contraction since it is not considered to be medically significant. At this point, the count (PRESS-COUNT) of the depressions of switch 14 is incremented and checked. When the count of switch 14 depressions reaches 3 (in a small time interval as described below), the status of the labor pain announcer feature of the labor pain timer mode is checked. If the labor pain announcer feature was previously turned on, it is turned off at this time and the display 20 is caused to present a display "Cd" to verify to the user that the labor pain announcer feature has been turned off. If the labor pain announcer feature was previously off (as is the case when the system 10 is initialized by cycling the power on and off through actuation of the power control switch 22), and if the timing switch 14 has been depressed three times quickly (in the short time interval mentioned above), then the labor pain announcer feature is turned on and the display 20 shows a display "CC" to verify to the user that the labor pain announcer feature has been activated. Following the tests and actions shown on page 8 of the PDL listing, control in the software program next proceeds to page 6 of the PDL listing to monitor the timing switch 14 and readout switch 18 for the next depression of either.

If a false contraction was not detected by ULN 98 on page 8 of the PDL listing (that is, the timing switch 14 was depressed for more than 23 seconds), ULN 111-124 are performed to compute the time length of the previous interval since the last measured contraction. A first time flag is used in ULN 112 to bypass this computation since there would be no previous contraction if the contraction just measured was the first contraction which occurred. If the contraction just measured was not the first contraction which occurred, the time interval (from the start of the previous measured contraction to the start of the contraction just measured) is computed from the times which have been stored in the random access memory of the processor U2, and the interval time is rounded to the nearest minute (or rounded to the nearest tenth of a minute if the interval is less than seven minutes long) and saved in the random access memory of the processor U2. Interval breaks which are longer than twenty minutes in length are not considered to be medically significant and are recorded in the memory of the processor U2 as an abbreviation "LG". The labor pain announcer feature of the labor pain timer mode may be used if the measured interval between contractions was less than five minutes. If the labor pain announcer feature is to be used, the length of the last time interval between contractions will have subtracted from it a predetermined anticipation time (preferably ten seconds), and will be used as the time to check in operation of the labor pain announcer feature. If the labor pain announcer feature is to be used, a flag (the READINESS-FLAG) is set as in ULN 105.

Once the interval processing shown in ULN 111-124 has been performed, the steps shown in ULN 125-131 are performed to round off the contraction time to the nearest second, save the measured contraction time in the random access memory of the microprocessor U2, and display the measured contraction time in the display 20 for four seconds. If the measured contraction time was longer than 99 seconds, the symbol "LG" is saved in the memory of processor U2 instead of the actual measured contraction time, but the display 20 will show the actual measured contraction time (or measured contraction time up to a maximum of 180 seconds). The clock timer of the software program is then reset to the time of the start of the previous contraction and the first time flag (the flag which is checked in ULN 112) is cleared. Processing by the software computer program in the processor U2 then continues with the steps shown on page 6 of the PDL listing.

The steps shown on page 6 of the PDL listing are performed when neither the timing switch 14 nor the readout button 18 is depressed, in particular following release of the timing switch 14. A pointer to the current memory item for the recorded time to be displayed on the display 20 (for the readout feature) is then reset to point to the most recent recorded duration (on line 2 of page 6). Next, a counter (on line 4 of page 6) is set to three to provide a means of resetting the readout pointer and switch actuation counter (PRESS-COUNT) after a predetermined amount of time elapses. The main processing loop is then entered, starting with line 6 on page 6. As long as the switches 14 and 18 are not depressed, the system 10 program remains in the loop just described.

The steps shown in lines 6-12 of page 6 describe two major functions. First, a decimal point on the display 20 is flashed every five seconds. Second, the "3" count is decremented. When the "3" count goes to zero (after the flashing of decimal point three times), the readout counter and press counter are each reset. The press count reset means that three depressions of the timing switch must occur in less than 15 seconds to toggle the readout announcer feature on and off.

Lines 13-18 then describe the checking of the various parameters to determine if the labor pain announcer should become active. In particular, the announcer mode must be turned on and current elapsed time must be greater than or equal to the previously computed announcer time. Page 11 describes the labor pain announcer action and will be discussed later.

If the announcer was not activated, the switches are next checked in lines 19-24. If the timing switch is on, processing continues with the logic previously discussed (PDL page 7). If the readout switch is depressed, processing continues on PDL page 10 with "Readout Data". If no switches are set, the loop is repeated starting with line 6.

READOUT FEATURE

Page 10 of the PDL describes the readout operation. First, an integral one second boundary is reached. The only purpose of this is to allow proper operation of the specific display routines used and has no real significance.

Lines 3-6 check whether it is the first time or the end of display readout memory was reached through prior display activity. If either is true, "nn" is displayed to indicate "none" or "no more" and an exit is made to the idle loop routine on page 6 of the PDL.

If not the end of data, lines 7-12 display a "dU" for duration or "In" for interval (depending on which parameter is next to be displayed), followed by a short pause. Note that the display alternately reads out labor pain durations and then intervals between them, starting with the most recent and working back in time until the end of recorded history (or end of available memory) is reached. Lines 14-20 first display the proper value from memory until the next integral second is reached. At this time the switches are checked. If the timing switch is on, an exit is made to page 7 of the PDL to monitor the new labor pain. If the readout switch is still set, the logic jumps to line 25 to check for the labor pain announcer time. If the readout switch was released, lines 22 and 23 are performed. This results in the display pointer being moved back to the next oldest entry and an exit to the idle loop routine on page 6.

Lines 26-31 describe the test for labor pain announcer. This is identical to the test on page 6, lines 13-18, and it will not be described again. If it is not time for the announcer, processing continues with a loop back to line 14 to display the current information some more. This loop continues as long as the readout switch is held down and no other event (such as a timing switch depression) occurs to interrupt the display loop.

LABOR PAIN ANNOUNCER FEATURE

When the time has elapsed, as previously described, to be 10 seconds less than the last recorded contraction interval, the logic on page 11 of the PDL is entered. Lines 1 and 2 first test if the announcer time was valid (less than five minutes and not already displayed). If not valid, an immediate exit back to page 6 of the PDL is made. Otherwise, the validity flag is cleared (so the announcement will not be repeated) and a time count of 10 is set on line 6.

Lines 7-18 describe the actions during the ten second count period. Essentially, a "C" is flashed twice per second (at a 4 Hz rate). This is followed, during the "off" time, by a check of the switches. If the timing switch is pressed, signaling the start of a new labor pain, an exit is made to page 7 to monitor it. After the ten seconds elapse, control returns to the idle loop routine one page 6 of the PDL.

LABOR PAIN REHEARSING MODE

This mode was entered following power up by depressing only the readout switch. Page 13 of the PDL listing describes the initialization of this feature. The rehearsing routines make use of an optional audible device A1 termed a "beeper" or "buzzer". There are three patterns which may be selected by the user corresponding roughly to early, middle and late labor. The buzzer A1 may be used with any of these. Line 2 initializes the pattern to "1" and the beeper A1 to "off".

Lines 4-16 describe the pattern selection logic. Essentially, the pattern type (P for normal, A for buzzer mode) and number (1, 2, or 3) are displayed as long as the readout switch is depressed. When the timing switch is simultaneously pressed, the buzzer mode is toggled off and on accompanied by a change of the display from P to A (or A to P) and a beep when it changes to an "A".

When the readout button 18 is released, a ten-second wait count is set up (line 18). During the ten-second period, the switches 14 and 18 are checked (lines 20-33). If the readout button 18 is depressed again, the pattern number is incremented and displayed again (lines 24-28) after which the ten-second counter will be reset to ten and the down count repeated. A loop back to line 4 is used to accomplish the display logic.

When ten seconds have elapsed with no switch depression, the current timer "seconds" count is captured and saved as a pseudorandom number to be used to augment the rehearsal durations and intervals (line 34). The pseudo random number so created acts as a substantially random augmentation signal which may be applied to the selected pattern so that the occurrence of simulated contractions will be realistic and will tend not to be anticipated by the expectant mother. Processing continues on page 14 of the PDL listing with the output of the simulated contraction.

On PDL page 14, the logic in lines 1-8 first loads the appropriate parameters (into a common memory area in the processor U2) corresponding to the pattern number last selected. Lines 10-15 then perform an alert that the contraction is about the start by flashing a "C" for four seconds along with the beeper if the buzzer mode was enabled. The duration to use is then fetched from memory and combined with the random number to be used as a duration length. The software program timer routine is reset to zero and a loop is entered to display time during the simulated contraction.

Lines 17-38 present the logic used to display the time every five seconds with decimal points flashed in between on integral second boundaries. In addition, the beeper sounds every fifteen seconds if it was enabled. If the readout switch is pressed, the simulated contraction stops and control returns to page 13 of the PDL, line 24, to change the pattern number. Finally, if the current time reaches the previously computed duration time, an exit is made to page 15 to await the interval length expiration before starting the next simulated contraction.

Page 15 of the PDL listing shows the logic when the simulated contraction is over. Lines 1-4 first signal the end of the contraction by flashing an "E" for two seconds and (if enabled) putting out a long beep. The memory pointer is then incremented to point to the interval time, this time fetched and combined with the random number, and the timer is reset to zero (lines 5-7). The loop consisting of lines 9-18 is then entered. This loop sequentially checks for readout switch pressed (with an exit to PDL page 13, line 24 if so), flashes a decimal point every five seconds, on the second, and checks for end of interval time.

When the interval is done, lines 20-24 increment the memory pointer to point to the next simulated contraction time. If the end of the stored constants has been reached, the random number is incremented by three and then adjusted to be between zero and nine. The memory pointer is then reset to the first stored duration time. In any case, the device continues with the output of the next simulated contraction on PDL page 14, line 10.

The sequence of simulated contractions and intervals is repeated as long as power is applied to the device. The user may change patterns at will as previously described.

FETUS MOVEMENT COUNTER MODE

This mode was entered following power up by depressing the readout and timing switches simultaneously.

Each time a fetal movement is felt, the expectant mother is to depress the timing switch. The device counts and accumulates these depressions. After a twenty-minute length of time, the ratio of movements per minute is computed and displayed. The display 20 is used in the fetus movement counter mode in order to display numbers representing the counting performed by the processor U2 in the form of the number of fetal movements measured by processor U2 per unit of time. The timing period may be stopped earlier if desired. Once stopped, the ratio may be re-displayed by again pressing the readout switch. An option is to use the buzzer to signal the passing of each minute and the end of the twenty minutes.

Page 17 of the PDL describes the initialization of this feature. Line 2 first sets the buzzer enabled and then displays "FA" as long as either the timing or readout switch is depressed. Once both switches are released, the display goes blank and a ten-second count is set up (lines 3-4). Lines 5-13 describe the activity during the ten-second wait. If the readout switch is pressed during this time, the buzzer option is turned off and a beep output to acknowledge the action. Once turned off, it cannot be turned on again for this mode without cycling power and starting over.

After the ten-second period is done, the count of timing switch depressions is cleared and processing continues on PDL page 18 with the counting of fetal movements. The elapsed number of minutes is displayed for a brief period (line 2). Lines 4-7 show the counting of timing switch depressions. Lines 8-10 test for early termination of the timing period. This is accomplished by pressing the readout and timing switches simultaneously. When this occurs, an exit is made to page 19 of the PDL. Otherwise, lines 11-19 describe the action when an integral minute has elapsed. If the time count is twenty minutes, the exit to PDL page 19 is taken. If the buzzer was not disabled, a short beep is output. Processing then loops to line 2 to display the new minute time.

If a minute did not elapse yet, a check for an integral multiple of ten seconds is made in lines 20-22. If the check proves true, the time is displayed (minutes elapsed) by looping back to line 2. If it was not a multiple of ten seconds, but was an intermediate five-second interval, lines 23-25 cause a decimal point to flash. Control then loops back to line 4 to await the next event.

When the fetus movement count time reaches twenty minutes (or is terminated early), page 19 of the PDL is entered. Lines 1-3 first signal the end of the timing period by beeping for a long interval (if the buzzer was not disabled). Lines 4-7 round the time to the nearest minute and assure that the minute count is at least one to provide a valid divisor for the ratio computation. The ratio is then computed. The computed ratio of fetal movements per unit time is an indicator of the apparent health of the unborn child. This is performed to the accuracy of tenths of movements per minute. Line 10 displays this computed ratio for four seconds. Note that ratios greater than 7.9 are displayed to the nearest whole number.

Lines 12-16 form a loop which has control until the readout switch is pressed. The switch depression causes a re-display of the previously computed ratio (at line 10). Power must be removed to exit from this loop.

BREASTFEEDING TIMER MODE

An optional mode which may be implemented with a computer program for use with the processor U2 in the hardware shown in FIGS. 1, 2a and 2b is a breastfeeding timer mode which acts to provide reminders to the mother during post-natal child care so that the child may be fed for predetermined time periods, as in compliance with medical instructions received from the doctor. The purpose of the breastfeeding mode is to present, in the display 20 (and optionally by actuating the buzzer A1), an indication reminder when feeding should end after the system 10 has been signaled that the breastfeeding has begun.

The breastfeeding timer mode may be included in a system 10 having the other modes discussed above and may be selected during the initialization of the system 10 by depressing the readout button 18 for three times in rapid succession, which also serves to signal to the system 10 that the breastfeeding has begun. The system 10 then (after selection of the breastfeeding timer mode) should display the preset feeding time duration (for example, twenty minutes) in the display 20 and allow the feeding time duration to be changed by the user through actuation of the readout button 18. For example, actuating the readout button 18 for a long depression would reduce the feeding time duration by one minute for each time that such a long depression were given by the user. Also, actuating the readout button 18 for a short depression would increase the feeding time duration by one minute for each time that such a short depression were given by the user. At the same time, the display 20 would show the feeding time duration as set by the user so that the user could operate the readout button 18 and display 20 in an interactive fashion to set the feeding time duration to accommodate medical requirements.

Approximately ten seconds after the last depression of the readout button 18 was made in order to set the feeding time duration, the feeding time monitoring would begin inside the system 10 by the sampling of time pulses on the timing circuit 26, and such a start of feeding time would be indicated by the display of the symbol "F" in the display 20. Thereafter, the elapsed feeding time (in minutes) is presented in the display 20 every ten seconds, with the presentation in the display 20 of a single decimal point on the five second mark between the full displays. Activation of the audible buzzer A1 may be selected and deselected by manual actuation of the timing switch 14 and readout button 18 so that audible indications may be selectively, automatically produced at one-minute intervals, at the end of the feeding time period, or not at all (silence). Ending of the feeding time period is indicated to the user by the display 20 (which may flash the symbol "E") and (optionally) by beeping of the buzzer A1 (as described above). The elapsed feeding time continues to be presented in the display 20 by the processor U2 after the expiration of the feeding time period so that the user may keep track of how long feeding has continued.

CHILDBIRTH RECORDED INSTRUCTION FEATURES

Optional childbirth recorded instruction features may be provided in the system 10 by the addition of display devices to U8 and U9 in order to make a seven character alphanumeric display and the addition of commercially available speech synthesizer integrated circuits connected to the processor U2 and to an audio speaker. The seven character display would be useable during the labor pain timer mode or contraction rehearsing mode in order to display alphabetic character strings of entire words, commonly accepted abbreviations, or recognizable abbreviations. It is preferable that approximately seven characters be provided in order that the display be readily understandable. The speech synthesizer circuitry would allow the system 10 to provide audible instructions to the expectant mother and her coach in order to supplement written and classroom instructions given. For example, audible instructions could be given during the labor pain timer mode by the processor U2 through the speech synthesizer circuitry in order to indicate to the expectant mother (a) when cleansing breaths should be taken at the beginning and end of each contraction, (b) the type of breathing which should be occuring at various stages, and (c) the proper breathing rate.

The seven character display would be constructed by connecting additional display devices in parallel with the devices U8 and U9 so that the additional display devices are multiplexed by connection to the unused outputs (R0, R1, R5 and R7) of the processor U2. The processor U2 would control the seven character display and the speech synthesis circuitry under program control by processing the data previously received and stored in memory by the processor U2 and sensing the inputs to the processor U2 in order to provide the proper output instructions to the expectant mother and coach.

THE OBJECT CODE LISTING

Also included as a part of this specification are five pages of computer printout sheets which form a hexadecimal listing of the object code computer program of this invention. The listing is made up of hexadecimal digits representing nibbles of the program content, with each two adjacent digits representing a byte. The object code listing is presented in a sequence of rows and columns in which each row is preceded at its left with a four digit row number corresponding to the address of the first byte in the row, and in which the addresses of the bytes in the rows increases from left to right, with adjacent bytes in the same row representing the contents of sequentially adjacent addresses. The addresses of memory contents represented in the object code listing increases from the top to the bottom of the columns.

The object code listing includes two sections entitled "MEMORY DUMP FOR EPROM1 (BASIC/PRACTICE)" and "MEMORY DUMP FOR EPROM2 (BASIC/FETAL MON)" which correspond to the program contents for embodiments of this invention which provide the labor pain timer mode and the contraction rehearsing mode, or the labor pain timer mode and the fetus movement counter mode, respectively.

Further included as a part of this specification is a one page hexadecimal listing (entitled "MEMORY DUMP FOR DISPLAY TRANSLATION EPROM") of the contents of the EPROM U3 used to drive the displays U8 and U9 based on the output of the processor U2. The format of the listing for memory U2 is the same as that described above for the object code program to be stored in the memory U1.

Alternative versions of the medical timer system 10 of this invention may be constructed by loading (into memory U1) one of the object code programs (entitled "MEMORY DUMP FOR REVISED EPROM 1 (BASIC/REHEARSAL)" and "MEMORY DUMP FOR REVISED EPROM 2 (BASIC/FETAL MON)") which are presented in a five-page computer program listing included as part of this specification, and which are functionally similar to the above-described programs excepting for the differences described below. The program labeled "MEMORY DUMP FOR REVISED EPROM 1 (BASIC/REHEARSAL)" includes the labor pain timing mode and the contraction rehearsing mode. The program labeled "MEMORY DUMP FOR REVISED EPROM 2 (BASIC/FETAL MON)" includes the labor pain timer mode and the fetus movement counter mode. These programs include computer code for activation of the audible buzzer A1 automatically upon entry to the labor pain timing mode so that an audible signal is produced every fifteen seconds during the time that a contraction is occuring, and so that the activation of the audible buzzer A1 may be deselected (and reselected) by actuation of the readout button 18 followed by actuation of the timing switch 14, so both switch 14 and button 18 are simultaneously actuated (which is acknowledged by an audible beep from buzzer A1). The busser A1 (if activated) serves to produce an audible noise to indicate the running time duration of the labor contraction. If the contraction announcer feature of the labor pain timing mode is selected, the buzzer A1 (when activated) will also be actuated by processor U2 to alert the expectant mother when a contraction is to be anticipated.

The "MEMORY DUMP FOR REVISED EPROM 1 (BASIC?REHEARSAL)" also includes code for actuation of the audible buzzer A1 automatically upon entry into the contraction rehearsing mode so that the buzzer A1 is actuated at the start of and the end of each simulated contraction, and so that the actuation of the buzzer A1 may be deselected (and reselected) by actuation of the readout button 18 followed by actuation of the timing switch 14 so that both switch 14 and button 18 are simultaneously actuated (which is acknowledged by an audible beep from buzzer A1).

The "MEMORY DUMP FOR REVISED EPROM 2 (BASIC/FETAL MON)" also includes code for actuation of the audible buzzer A1 automatically upon entry into the fetus movement counter mode so that the buzzer A1 is actuated when the predetermined counting time period (twenty minutes) has elapsed, and so that activation of the audible buzzer A1 may be deselected during the first ten seconds of the counting time period by actuation of the readout button 18 followed by actuation of the timing switch 14 so that both switch 14 and button 18 are simultaneously actuated.

What is claimed is:

1. A labor contraction duration and interval timer comprising:
   a timing circuit that produces a timing signal;
   an electrical input device having a first state and a second state;
   a processor connected to said timing circuit and to said electrical input device, wherein:

said processor samples said timing signal when said input device is changed from the first state to the second state at the beginning of a contraction, and again samples said timing signal when said input device is changed from the second to the first state at the end of a contraction, and said processor automatically determines the length of time between the most recent input device state changes after the input device is changed from the second state to the first state, which time is the length of the measured contraction; and said processor additionally automatically determines the length of time between the two most recent changes of the input device from the first state to the second state, after the input device is changed from the first state to the second state, which time is the length of time between the beginning of one measured contraction and the beginning of the next measured contraction, or contraction interval; and a device for reading out the determined contraction length and contraction interval data.

2. The labor contraction duration and interval timer defined in claim 1, wherein said electrical input device comprises an electrical switch having a first position corresponding to said first state and a second position corresponding to said second state.

3. The labor contraction duration and interval timer defined in claim 2, wherein said switch comprises a push button timing switch that is lockable in said second state to facilitate the timing of the length of a contraction.

4. The labor contraction duration and interval timer defined in claim 1, additionally comprising a memory for storing contraction length data and contraction interval data.

5. The labor contraction duration and interval timer defined in claim 4, wherein said processor does not record contractions having a duration less than a pre-defined minimum duration.

6. The labor contraction duration and interval timer defined in claim 2, wherein said processor does not record the length of contraction intervals longer than a pre-determined maximum duration.

7. The labor contraction duration and interval timer defined in claim 2, wherein said processor analyzes the durations of measured contractions and the measured contraction intervals, to determine the expected length of the interval between labor contractions, and said processor produces a signal at a pre-determined time prior to the end of the expected time between labor contractions to announce when a contraction is to be expected.

8. A labor contraction rehearsal device comprising:
a timing circuit that produces a timing signal;
a memory storing a pattern of simulated labor contractions said stored pattern representing a series of time intervals between each simulated contraction and the time duration corresponding to each of the simulated contractions;
a processor coupled to said timing circuit and responsive to the pattern of contractions stored in said memory to produce a signal at the beginning and at the end of each simulated contraction, said processor acting to automatically change the simulated contraction pattern; and
an indicator responsive to said processor contraction signal to provide an indication of the beginning and of the end of each simulated contraction.

9. The labor contraction rehearsal device defined in claim 8, wherein said processor includes a randomizer to supply a substantially random augmentation signal to said pattern of contractions to modify said pattern.

10. The labor contraction rehearsal device defined in claim 9, wherein said randomizer comprises a switch connected to said processor so actuation of said switch causes said processor to sample said timing signal to provide a pseudorandom number as said substantially random augmentation signal.

11. The labor contraction rehearsal device defined in claim 8, wherein said memory stores a plurality of labor contraction patterns, and additionally comprising a selector coupled to said memory and to said processor for selecting one of said plurality of patterns.

12. A labor contraction duration and interval timer and rehearsal device comprising:
a timing circuit that produces a timing signal;
an electrical input device having a first state and a second state;
a memory for storing at least one pre-selected pattern of labor contractions;
a processor coupled to said timing circuit and to said electrical input device, wherein:
said processor samples said timing signal when said input device is changed from the first state to the second state at the beginning of a contraction, and again samples said timing signal when said input device is changed from the second state to the first state at the end of a contraction, and said processor automatically determines the length of time between the most recent input device state changes, after the input device has changed from the second state to the first state, which time is the length of the measured contraction;
said processor determines the time between the two most recent input device first state to second state changes, after the input device has changed from the first state to the second state, which is the length of time between the beginning of one measured contraction and the beginning of the next contraction or contraction interval; and
in the contraction rehearsal mode said processor is responsive to the pattern of contractions and stored in said memory to produce a contraction signal at each time that a contraction is to occur; and
a readout device for reading out the determined contraction length and contraction interval data; and
an indicator responsive to said processor contraction signal.

13. The labor contraction duration and interval timer and rehearsal device defined in claim 12, additionally comprising a randomizer coupled to said processor to provide a substantially random augmentation signal to said pattern of labor contractions to modify said labor contraction pattern.

14. The labor contraction duration and interval timer and rehearsal device defined in claim 13, wherein said randomizer comprises a switch coupled to said processor so that actuation of said switch causes said processor to sample said timing signal to provide a pseudorandom number as said substantially random augmentation signal.

15. The labor contraction duration and interval timer and rehearsal device defined in claim 12, wherein:
said processor produces a first contraction signal responsive to the stored pattern of contractions when a simulated contraction is to begin, and a second contraction signal responsive to the stored pattern of contractions when a simulated contraction is to end; and said indicator produces a first indication in response to said first contraction signal and a second indication in response to said second contraction signal.

16. The labor contraction duration and interval timer and rehearsal device defined in claim 12, wherein said processor stores the durations of recorded contractions and the intervals between recorded contractions and analyzes such contraction length data and contraction interval data to determine the expected length of the interval between contractions, and said processor produces a signal at a pre-determined anticipation time prior to the end of the expected time interval between contractions to announce when a contraction can be expected, if the expected time between contractions is less than a predetermined time.

17. A labor contraction duration and interval timer comprising:
   a timing circuit that produces a timing signal;
   means for sampling said timing signal at the beginning of a contraction and again at the end of a contraction;
   a processor coupled to said sampling means to determine the length of each measured contraction and the intervals between contractions; and
   a memory for storing the determined contraction length data and contraction interval data, wherein:
      said processor analyzes the stored contraction length data and contraction interval data to determine the expected length of the interval between contractions, and said processor produces a signal at a pre-determined time prior to the end of the expected contraction interval to announce when a contraction is to be expected.

18. A labor contraction duration and interval timer and rehearsal device comprising:
   a timing circuit that produces a timing signal;
   means for sampling said timing signal at the beginning of a contraction and again at the end of a contraction;
   a processor coupled to said sampling means for determining the length of each measured contraction and the intervals between contractions; and
   a memory for storing the determined contraction length data and contraction interval data, and for storing at least one pre-selected pattern of labor contractions, wherein:
      said processor analyzes the stored contraction length data and contraction interval data to determine the expected length of the interval between contractions, and said processor produces a signal at a pre-determined time prior to the end of the expected contraction interval to announce when a contraction is to be expected; and
      said processor is responsive to the pattern of contractions stored in said memory to produce a contraction signal when a simulated contraction is to occur.

19. The labor contraction duration and interval timer and rehearsal device defined in claim 18, additionally comprising a randomizer coupled to said processor to supply a substantially random augmentation signal to said stored pre-selected pattern of contractions to modify said pattern.

20. A labor contraction duration and interval timer and rehearsal device comprising:
   a timing circuit that produces a timing signal;
   means for sampling said timing signal at the beginning of a contraction and again at the end of a contraction;
   a processor coupled to said sampling means for determining the length of each measured contraction and the intervals between contractions;
   a memory for storing the determined contraction length data and contraction interval data, and for storing at least one pre-selected pattern of labor contractions; and
   a randomizer coupled to said processor to add a substantially random augmentation signal to said stored pre-selected pattern of contractions to modify said pattern, wherein:
      said processor is responsive to the modified pattern of contractions to produce a contraction signal when a simulated contraction is to occur.

* * * * *